United States Patent [19]

Metcalf et al.

[11] 4,088,668
[45] May 9, 1978

[54] ACETYLENE DERIVATIVES

[75] Inventors: Brian Walter Metcalf, Strasbourg; Michel Jung, Illkirch Graffenstaden, both of France

[73] Assignee: Merrell Toraude et Compagnie, Strasbourg, France

[21] Appl. No.: 812,068

[22] Filed: Jul. 1, 1977

[51] Int. Cl.² .............................................. C07F 7/10
[52] U.S. Cl. ......................... 260/448.2 N; 260/346.73; 260/448.2 F; 424/184
[58] Field of Search .................. 260/448.2 N, 346.1 R

[56] References Cited

U.S. PATENT DOCUMENTS 3,946,060  3/1976  Metcalf et al. .............. 260/448.2 N

*Primary Examiner*—Paul F. Shaver

*Attorney, Agent, or Firm*—L. Ruth Hattan; Eugene O. Retter; George W. Rauchfuss, Jr.

[57] ABSTRACT

Novel compounds of the following general formula are useful pharmacologic agents and are useful as intermediates for the preparation of pharmacologically useful compounds.

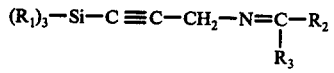

wherein $R_1$ is a straight or branched lower alkyl group having from 1 to 4 carbon atoms, $R_2$ is trialkylmethyl, phenyl, 1-adamantanyl or 2-furyl, $R_3$ is methoxy or ethoxy; and acid addition salts thereof.

5 Claims, No Drawings

ACETYLENE DERIVATIVES

FIELD OF INVENTION

This invention relates to novel acetylene derivatives.

BACKGROUND OF INVENTION

Compounds of the following structure are described in U.S. Pat. No. 3,946,060 issued Mar. 23, 1976, as useful intermediates and as monamine oxidase inhibitors;

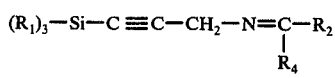

wherein $R_1$ is lower alkyl of from 1 to 4 carbon atoms; $R_2$ is hydrogen or phenyl; and $R_4$ is phenyl or trialkylmethyl wherein the alkyl moiety has 1 or 2 carbon atoms.

The compounds of the present invention are distinguishable from the above compounds in that they are carboximidates in that the imine forming carbon atom is substituted with a methoxy or ethoxy group. The compounds of the present invention offer certain advantages over the compounds of the above structure as useful intermediates in that they react with greater regiospecificity resulting in better yields of product. For example, it has been found that the compounds of the present invention result in higher yields of the ornithine derivatives described hereinbelow in Formula III.

SUMMARY OF INVENTION

Compounds of the following general Formula I are useful as slow releasing forms of monoamine oxidase inhibitors leading to longer duration of activity and are useful as intermediates for the preparation of pharmacologically useful compounds.

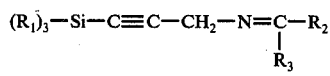

Formula I

In the above Formula I, $R_1$ is a straight or branched lower alkyl group having from 1 to 4 carbon atoms; $R_2$ is trialkylmethyl wherein the alkyl moiety has one or two carbon atoms, phenyl, 1-adamantanyl or 2-furyl; and $R_3$ is methoxy or ethoxy. Acid addition salts of the compounds of Formula I are also included in this invention.

DETAILED DESCRIPTION OF INVENTION

In the above general Formula I, straight or branched lower alkyl groups of from 1 to 4 carbon atoms which $R_1$ may be are illustrated by methyl, ethyl, n-propyl, n-butyl, isopropyl and tert-butyl.

In the above general Formula I, the trialkylmethyl groups which $R_2$ may represent are tert-butyl and triethylmethyl.

Acid addition salts of the compounds of this invention include those of pharmaceutically acceptable inorganic or organic acids. Suitable inorganic acids are, for example, hydrochloric, hydrobromic, sulfuric or phosphoric acids. Suitable organic acids are, for example, lactic, malonic, maleic, salicyclic, tartaric, citric or ascorbic acids.

The compounds of general Formula I are useful as intermediates in the preparation of compounds of the following Formula II which compounds are useful as sedatives or γ-aminobutyric acid transaminase inhibitors as described in U.S. Pat. No. 3,959,356 issued May 25, 1976, and of compounds of the following general Formula III which are useful as irreversible inhibitors of the decarboxylases of ornithine, S-adenosylmethionine and methionine and as antiinfective agents, particularly antibacterial and antiviral agents as described in copending U.S. application Ser. No. 812,067 filed concurrently herewith:

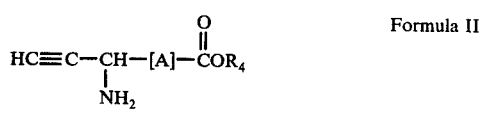

Formula II wherein $R_4$ represents hydroxy, an alkoxy group or an amide function; [A] represents

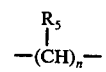

or $-CH=CH-$ wherein $R_5$ represents hydrogen, a lower alkyl group, phenyl and substituted phenyl; and $n$ is an integer of from 1 to 5.

Formula III wherein Z is β-methylthioethyl, β-benzylthioethyl, S-(5'-desoxyadenosin-5'-yl)-S-methylthioethyl, γ-guanidinopropyl, or $RHN(CH_2)_n-$; $n$ is the integer 3 or 4; each R is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched, or

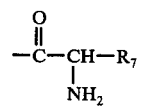

wherein $R_7$ is hydrogen, a straight or branched lower alkyl group of from 1 to 4 carbon atoms, benzyl or p-hydroxybenzyl; $R_6$ is hydroxy, a straight or branched alkoxy group of from 1 to 8 carbon atoms, $-NYY'$ wherein each of Y and Y' is hydrogen or a lower alkyl group of from 1 to 4 carbon atoms, or

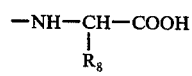

wherein $R_8$ is hydrogen, a straight or branched lower alkyl group of from 1 to 4 carbon atoms, benzyl or p-hydroxybenzyl.

The compounds of general Formula I are also useful as monoamine oxidase inhibitors rendering them useful in treating mental depression and hypertension.

As pharmacologic agents the compounds of this invention can be administered orally or parenterally to animals, particularly warm blooded animals and mammals, either alone or in the form of pharmaceutical preparations containing as the active ingredient a compound of general Formula I to achieve the desired effect. Pharmaceutical preparations containing compounds of this invention and conventional pharmaceutical carriers can be employed in unit dosage forms, such as, solids, for example, tablets, pills and capsules or liquid solutions, suspensions or elixirs for oral administration, or liquid solutions, suspensions and emulsions for parenteral use. The quantity of compound administered can vary over a wide range to provide from 0.1 to 200 mg/kg (milligram per kilogram) of body weight of the patient per day. Unit doses of these compounds can contain from about 50 to 200 mg of the compound and may be administered, for example, from 1 to 4 times daily.

The preferred compound of this invention is methyl N-(3-trimethylsilylprop-2-ynyl)benzenecarboximidate having the structure:

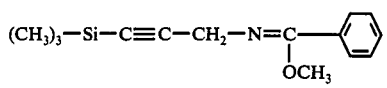

The compounds of this invention are prepared by reacting propargylamine, wherein the acetylene function is protected by a trialkylsilyl group, with benzoyl chloride, pivalic acid chloride, 2,2-diethylbutyric acid chloride, 2-furoic acid chloride or 1-adamantancarboxylic acid chloride at about 0° C in diethyl ether, dioxane, tetrahydrofuran, chloroform, methylenechloride, dimethylformamide, dimethyl acetamide or chlorobenzene in the presence of an organic base, such as trialkylamine, for example, triethylamine, pyridine or an equivalent base after which the reaction mixture is allowed to warm to room temperature, or about 25° C for 1 hour. The resulting amide derivative is combined with an alkylating reagent, such as, methylfluorosulfonate, dimethylsulfate, methyliodide, methyl p-toluenesulfonate or trimethyloxonium hexafluorophosphate when $R_3$ is methoxy and triethyloxonium tetrafluoroborate when $R_3$ is ethoxy at about 25° C in a chlorinated hydrocarbon solvent such as methylene chloride, chlorobenzene or chloroform and the reaction mixture is refluxed overnight, or for about 12 to 20 hours. The mixture is then cooled to about 25° C, and an organic base, such as triethylamine or pyridine is added after which the solution is extracted with brine and the product isolated.

The protected propargylamine starting material is obtained by treating 3-trialkylsilylprop-2-ynyl-1-iminobenzyl with hydrazine or phenylhydrazine at about 25° C for about ½ hour after which the mixture is diluted with, for example, petroleum ether, benzene or toluene and the iminobenzyl derivative isolated. Alternatively treatment with 0.5 to 1 N HCl gives the hydrochloride.

The 3-trialkylsilylprop-2-ynyl-1-iminobenzyl derivative is obtained from propargylamine by forming in a known manner a Schiff's base with benzaldehyde and reacting said Schiff's base with a base such as an alkyl Grignard or alkyl lithium followed with an appropriate trialkylsilylchloride, for example, trimethylsilylchloride or dimethyltert-butylsilyl chloride in a known manner (E. J. Corey and H. A. Kirst, Tetrahedron Letters, 1968, 5041).

The following examples further illustrate the preparation of the compounds of this invention.

EXAMPLE 1

Prop-2-ynyl-1-iminobenzyl

A solution of propargylamine (26.1 g, 0.47 M) and benzaldehyde (52 g, 0.49 M) in benzene (150 ml) is treated with $MgSO_4$ (20 g). The reaction mixture is stirred at room temperature for 30 minutes, then filtered. Excess water is removed by way of azeotropic distillation, the solution concentrated, and the residue distilled to give prop-2-ynyl-1-iminobenzyl (55.5 g, 82%) b.p. 107°-110° C (10 mm Hg).

EXAMPLE 2

3-Trimethylsilylprop-2-ynyl-1-iminobenzyl

To a mechanically stirred solution of prop-2-ynyl-1-iminobenzyl (43.5 g, 0.30 M) in tetrahydrofuran (400 ml) at 0° C is added, during 30 minutes, ethyl magnesium bromide (285 ml of a 1.12 M solution, 0.316 M). After 30 minutes at 0° C, the resulting solution is treated with a solution of trimethylsilylchloride (32.4 g, 0.30 M) in tetrahydrofuran (100 ml), the addition taking 45 minutes. After stirring at 0° C for an additional 1½ hours, the solution is treated with brine. The organic phase is separated and washed with brine (8 × 100 ml), then dried and concentrated on a rotorvapor. The residue is distilled to afford a liquid (52.2 g, 80%) b.p. 91°-100° C, 0.6 mm Hg. An aliquot was redistilled to give 3-trimethylsilylprop-2-ynyl-1-iminobenzyl.

By substituting appropriate amounts of triethylsilylchloride or other tri-(higher) alkylsilyl chlorides in place of trimethylsilylchloride the respective 3-triethylsilylprop-2-ynyl-1-iminobenzyl or other 3-tri(higher) alkylsilylprop-2-ynyl-1-iminobenzyl derivatives wherein the alkyl moiety is straight or branched are obtained.

EXAMPLE 3

3-Trimethylsilylprop-2-ynylamine

At room temperature 12.54 g (0.050 M) of 3-trimethylsilylprop-2-ynyl-1-iminobenzyl is treated with 7.1 g (0.07 M) of phenylhydrazine. After ½ hour the mixture is diluted with 200 ml of petroleum ether (b.p. 30°-60° C) and filtered. The filtrate is concentrated and distilled to give 3-trimethylsilylprop-2-ynylamine as a liquid, b.p. 55° C/15 mm.

EXAMPLE 4

N-(3-Trimethylsilylprop-2-ynyl)benzamide

To 8.2 g (0.07 M) of 3-trimethylsilylprop-1-ynylamine in 150 ml of diethyl ether containing 6.6 g (9.1 ml) of triethylamine at 0° C is added 9.1 g (0.07 M) of benzoyl chloride in 30 ml of ether. After 1 hour at 25° C the solution is washed well with brine and the ether extract dried over magnesium sulfate, filtered and the filtrate concentrated. The residue is recrystallized from methanol to give N-(3-trimethylsilylprop-2-ynyl)benzamide.

When in the procedure of Example 4 an appropriate amount of pivalic acid chloride, 2,2-diethylbutyric acid chloride, 1-adamantanylcarboxylic acid chloride or 2-furoic acid chloride is substituted for benzoyl chloride the following respective products are obtained:

N-(3-trimethylsilylprop-2-ynyl)-2,2-dimethylpropionamide,

N-(3-trimethylsilylprop-2-ynyl)-2,2-diethylbutyramide,

N-(3-trimethylsilylprop-2-ynyl)-1-adamantancarboxamide and
N-(3-trimethylsilylprop-2-ynyl)-2-furancarboxamide.

EXAMPLE 5

Methyl N-(3trimethylsilylprop-2-ynyl)benzene carboximidate

To 9.7 g (0.04 M) of N-(3-trimethylsilylprop-2-ynyl)-benzamide in 100 ml of methylene chloride at 25° C is added 4.8 g (3.4 ml, 0.04 M) of methylfluorosulfonate. The solution is refluxed for about 12 hours, and on cooling to room temperature 4.25 g (0.04 M) of triethylamine is added. The mixture is extracted with brine, dried over magnesium sulfate, filtered, and the filtrate is evaporated. The residue is distilled, a fraction 85°–105° (0.1 mm), 4.6 g being collected.

When in the procedure of Example 5 an appropriate amount of N-(3-trimethylsilylprop-2-ynyl)-2,2-dimethylpropionamide, N-(3-trimethylsilylprop-2-ynyl)-2,2-diethylbutyramide, N-(3-trimethylsilylprop-2-ynyl)-1-adamantancarboxamide or N-(3-trimethylsilylprop-2-ynyl)-2-furancarboxamide is substituted for N-(3-trimethylsilylprop-2-ynyl)benzamide the following respective products are obtained:

methyl N-(3-trimethylsilylprop-2-ynyl)-tert-butylcarboximidate,
methyl N-(3-trimethylsilylprop-2-ynyl)triethylmethylcarboximidate,
methyl N-(3-trimethylsilylprop-2-ynyl)-1-adamantancarboximidate, and
methyl N-(3-trimethylsilylprop-2-ynyl)-2-furancarboximidate.

EXAMPLE 6

Ethyl N-(3-trimethylsilylprop-2-ynyl)benzene carboximidate

When in the procedure of Example 5 an appropriate amount of triethyloxonium tetrafluoroborate is substituted for methylfluorosulfonate, ethyl N-(3-trimethylsilylprop-2-ynyl)benzene carboximidate is obtained.

The following example illustrates the utility of the presently claimed compounds as intermediates.

α-Acetylene-α,δ-diaminovaleric acid 11.8 g (0.048 M) of N-(3-Trimethylsilylprop-2-ynyl)-benzenecarboximidate in 20 ml of tetrahydrofuran is added to lithium diisopropylamide, prepared from 4.9 g (6.78 ml, 0.048 M) of diisopropylamide in 60 ml of tetrahydrofuran and 23.6 ml of a 2.05 M solution of n-butyllithium at −70° C after which 9.5 g (0.042 M) of N-(3-bromopropyl)benzylimine is added, and the mixture is stirred at −70° C for 5½ hours. To the reaction mixture is added 23.6 ml of a 2.05 M solution of n-butyllithium followed by the addition of 4.5 g (3.67 ml, 0.043 M) of methyl chloroformate. After 30 minutes at −78° C the mixture is treated with brine, and the reaction product is isolated by ether extraction. The ether extract is evaporated and 300 ml of 3 N HCl is added to the resulting residue and the mixture is refluxed for 7 hours. On cooling the mixture is washed well with methylene chloride, made alkaline and washed again. The aqueous solution is acidified and concentrated to dryness. The residue is triturated with ethanol, filtered and the ethanol evaporated. The residue is dissolved in water, the pH adjusted to 6, and the solution is applied to a column of Amberlite 120 H⁺, eluting with 1 M NH₄OH which affords, upon recrystallization from ethanol-water, α-acetylene-α, δ-diaminovaleric acid, M.P. 168°–169° (dec.).

We claim:

1. A compound of the formula

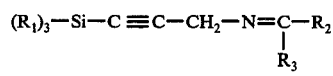

wherein $R_1$ is a straight or branched lower alkyl group having from 1 to 4 carbon atoms; $R_2$ is trialkylmethyl wherein the alkyl moiety has 1 or 2 carbon atoms, phenyl, 1-adamantanyl or 2-furyl; and $R_3$ is methoxy or ethoxy and acid addition salts thereof.

2. A compound of claim 1 wherein $R_1$ is methyl.
3. A compound of claim 1 wherein $R_2$ is phenyl.
4. A compound of claim 1 which is:

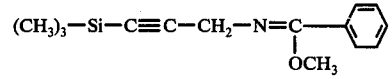

5. A process for preparing a compound of claim 1 which comprises the steps of reacting propargylamine, wherein the acetylene function is protected by a trialkylsilyl group, with benzoyl chloride, pivalic acid chloride, 2,2-diethylbutyric acid chloride, 2-furoic acid chloride or 1-adamantanecarboxylic acid chloride at about 0° C in an appropriate solvent in the presence of an organic base after which the reaction mixture is allowed to warm to about 25° C for 1 hour, combining the resulting amide derivative with an appropriate alkylating reagent at about 25° C in an appropriate solvent after which the reaction mixture is refluxed for from 12 to 20 hours, cooling the reaction mixture to about 25° C after which an organic base is added and extracting the mixture with brine.

* * * * *